United States Patent
Gunning et al.

(10) Patent No.: US 7,619,235 B2
(45) Date of Patent: Nov. 17, 2009

(54) OPTICAL SAMPLING ARRANGEMENTS

(75) Inventors: Mark Julian Gunning, Tadworth (GB); Graham Poulter, Orpington (GB)

(73) Assignee: Smiths Group PLC, London (GB)

( * ) Notice: Subject to any disclaimer, the term of this patent is extended or adjusted under 35 U.S.C. 154(b) by 0 days.

(21) Appl. No.: 11/542,178

(22) Filed: Oct. 4, 2006

(65) Prior Publication Data
US 2007/0075281 A1   Apr. 5, 2007

(30) Foreign Application Priority Data
Oct. 5, 2005   (GB)   ................................. 0520207.2

(51) Int. Cl.
*H01J 3/14*   (2006.01)
*G01N 21/49*   (2006.01)

(52) U.S. Cl. .................. 250/573; 250/576; 250/216

(58) Field of Classification Search ......... 250/573–577, 250/338.1, 239, 227.24, 227.25, 216; 356/436–442, 356/244, 246
See application file for complete search history.

(56) References Cited

U.S. PATENT DOCUMENTS

| | | | | |
|---|---|---|---|---|
| 3,961,346 A | * | 6/1976 | White | .................. 356/244 |
| 4,003,661 A | * | 1/1977 | Yamano | ..................... 356/436 |
| 4,980,551 A | * | 12/1990 | Wong | ....................... 250/338.1 |
| 5,923,031 A | * | 7/1999 | Naya | ..................... 250/227.25 |
| 6,531,702 B1 | * | 3/2003 | Mischler et al. | ........ 250/339.12 |
| 2003/0180191 A1 | * | 9/2003 | Suzuki et al. | ............... 422/102 |

FOREIGN PATENT DOCUMENTS

EP   0 436 338 A2   7/1991
JP   55116243 A   *   9/1980

OTHER PUBLICATIONS

Infrared Window Materials, http://infrared.als.lbl.gov/IRwindows.html.*

* cited by examiner

*Primary Examiner*—Que T Le
*Assistant Examiner*—Jennifer Bennett
(74) *Attorney, Agent, or Firm*—Foley & Lardner LLP

(57) ABSTRACT

An infra-red liquid sampling cell has a sapphire base plate with a part-spherical concave recess. A sapphire upper plate is hinged relative to the base plate larger radius of curvature than the recess. When the upper plate is lowered into contact with the base plate its convex surface contacts the liquid sample thereby excluding air bubbles and, when in contact with the edge of the recess, produces a well-defined sample thickness. An infra-red source directs radiation down through both plates and the liquid sample to a detector.

28 Claims, 4 Drawing Sheets

OPTICAL SAMPLING ARRANGEMENTS

BACKGROUND OF THE INVENTION

This invention relates to optical sampling arrangements and to spectroscopic apparatus including such arrangements.

Where optical measurements, such as for spectroscopic purposes, need to be made on liquid samples, the sample is usually placed in a transmission liquid cell 1 of the kind shown in FIG. 1. The cell 1 consists of two windows 2 and 3, which are optically transparent to the wavelengths of interest, and which are separated by a spacer 4. The cell 1 is placed in the optical path between a source of optical radiation 5 and a radiation detector 6. The sample 7 to be measured is contained in the cavity 8 between the windows 2 and 3. The pathlength of the cell 1 is determined by the thickness of the spacer 4 and this is arranged to be sufficient so that the sample 7 absorbs a measurable amount of the optical radiation at the wavelengths of interest. The pathlength can vary from several millimetres in the UV and visible regions to just microns in the mid-infrared region.

These liquid transmission cells are widely used but suffer from a number of disadvantages. They can be difficult to fill and are prone to trapping air bubbles, which can prevent accurate measurements being made. Shorter pathlengths, as needed for near and mid-infrared radiation, can be particularly difficult to provide when used with viscous samples. The cells can be very difficult to clean, especially with viscous or sticky samples. This often requires the entire cell to be disassembled and significant quantities of solvent may be needed, which are often flammable or hazardous. The cells usually have a large number of parts, which have to be correctly aligned and assembled to ensure they do not leak. It can also be difficult accurately to reproduce the pathlength when the cell has to be taken apart and rebuilt, such as after cleaning. This is a particular problem when making quantative measurements. Furthermore, the relatively large size of the cell and the large number of components can make it difficult to control or stabilize the temperature of the cell.

BRIEF SUMMARY OF THE INVENTION

It is an object of the present invention to provide an alternative form of optical sampling arrangement and spectroscopic apparatus.

According to one aspect of the present invention there is provided an optical sampling arrangement including a first element having an upper surface with a smoothly curved concave cavity in which a liquid sample can be placed and a second element having a lower surface with a smoothly curved convex formation adapted to locate with the cavity and contact an upper surface of the liquid sample in the cavity, the curvature of the convex formation being shallower than that of the concave cavity, and at least one of the first and second elements being transparent to optical radiation such that optical radiation can be directed through the thickness of the liquid sample.

Preferably both the first and second elements are optically transparent. The cavity is preferably circular in the plane of the upper surface of the first element. The first and second elements may contact one another along a line of contact at the intersection of the cavity with the upper surface. Alternatively, the upper surface of the first element may be provided with a contact land around the cavity having a curvature parallel with that of the convex formation such that the convex formation makes contact with the land. The first element may have a lower surface that is flat and parallel with the upper surface. Alternatively, the first element could have a lower surface provided with angled faces. The arrangement may include a source of radiation arranged to direct radiation into one of the angled faces at an angle to the normal to the face. The arrangement may include a radiation detector arranged to receive radiation transmitted through an angled face at an angle to the normal to the face. Alternatively, the first element may have a lower surface with a curved profile. The upper surface of the second element may be flat. Alternatively, it may have a curved profile and its upper surface may be concave with the same centre of curvature as the convex surface on the lower surface of the second element. The first element is preferably mounted below the second element in a fixed position, the second element being movable up and down relative to the first element. The second element may be hinged relative to the first element. The surfaces of both the first and second elements are preferably transparent. Alternatively, one of the elements could have a reflective layer on an outer surface arranged to reflect optical radiation back through the element. The second element may have a reflective surface arranged to reflect optical radiation passing through the first element from below and through the sample back down through the sample and the first element. The optical radiation is preferably in the near infra-red region. One or both elements may be of sapphire. The concave cavity and the convex surface formation are preferably part spherical.

According to another aspect of the present invention there is provided spectroscopic apparatus including a source of optical radiation, a radiation detector and an optical sampling arrangement according to the above one aspect of the present invention located in the optical path between the source and the detector.

The source of optical radiation is preferably in the near infra-red and the detector is responsive to radiation in the near infra-red. The source and detector may be located on opposite sides of the optical sampling arrangement or on the same side. The apparatus may include a housing containing the source and detector, the first element being sealed in an upper surface of the housing.

Apparatus including a spectroscopic liquid sampling cell according to the present invention will now be described, by way of example, with reference to the accompanying drawings.

BRIEF DESCRIPTION OF THE ACCOMPANYING DRAWINGS

DETAILED DESCRIPTION OF THE PREFERRED EMBODIMENTS

Figure 1:
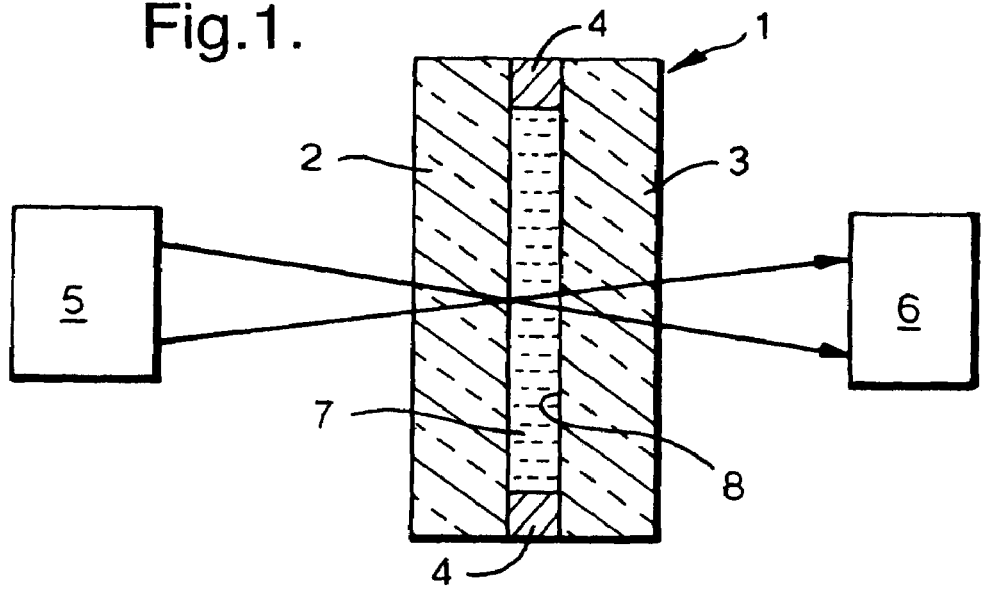
FIG. 1 is a schematic, side elevation view of prior art spectroscopic apparatus including a liquid sampling cell.
Figure 2:
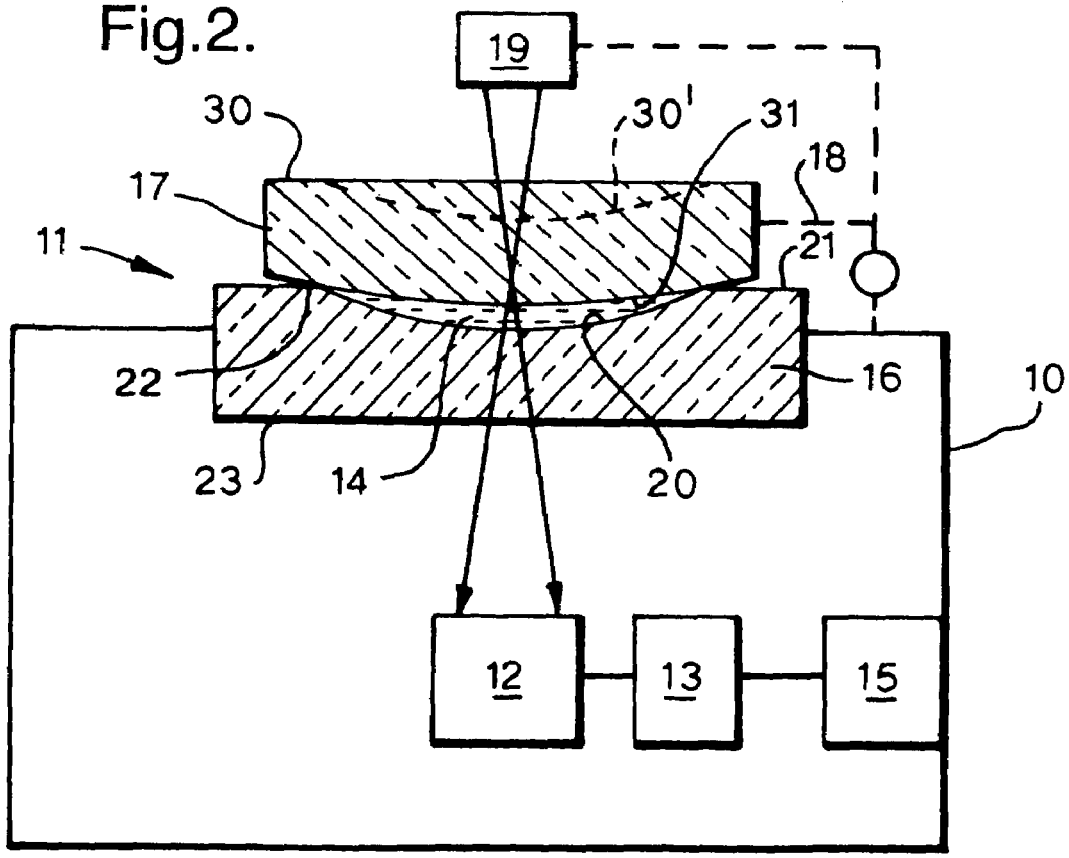
FIG. 2 is a schematic, side elevation view of a first embodiment of spectroscopic apparatus according to the present invention.
Figure 3:
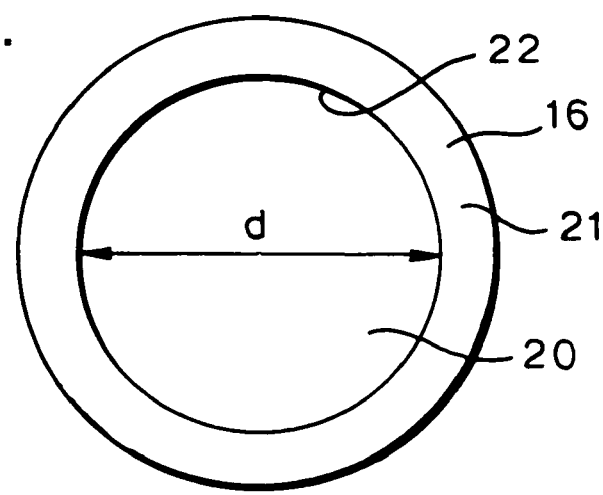
FIG. 3 is a plan view of the lower part of the sampling cell shown in FIG. 2.

With reference first to FIGS. 2 and 3, the spectroscopic apparatus includes a housing 10 supporting a liquid sampling cell 11 on its upper surface and containing an optical detector 12 within it, mounted directly below the cell. The detector 12 provides an output to a processor 13, which, in turn provides an output representation of the nature of the liquid 14 in the cell 11 to utilisation means, such as a display 15. The cell 11 comprises a lower element or base plate 16, fixed with the upper surface of the housing 10. The cell 11 also includes an upper element or plate 17 mounted on an arm 18, which is hinged on the housing 10 so that it can be raised to lift the upper plate away from the lower plate 16 and can be lowered to press the upper plate into contact with the lower plate. The arm 18 also supports a source 19 of optical radiation in the near infrared region. The radiation produced by the source 19 is directed downwardly through the upper plate 17, through the thickness of the liquid sample 14 and the lower plate 16 to the detector 12. As shown, radiation from the source 19 is focussed, such as by a converging lens (not shown), but the radiation could, instead, be collimated. Only radiation passing through the central region of the cell 11 is detected to ensure that variation in path length across the cell does not introduce a significant measurement error. The upper and lower plates 17 and 16 are both circular and are made of a material that is both transparent to the radiation and is not damaged by the range of substances with which the apparatus is to be used. A preferred material is sapphire but other materials may be possible.

The liquid sample 14 is contained within a cavity 20 located centrally in the upper surface 21 of the lower plate 16. The cavity 20 is concave and is smoothly curved over its entire surface. As shown in FIG. 3, the cavity 20 is circular in the plane of the upper surface 21 and typically has a diameter "d" of about 8 mm. The profile of the cavity 20 is part spherical with a radius of curvature of about 9.3 mm, the centre of curvature being located perpendicularly above the plane of the flat part of the upper surface 21 by a distance of about 8.4mm, giving a depth of cavity at its centre, when open, of about 0.9 mm. The edge of the cavity 20 meets the upper surface 21 of the plate 16 at a sharp edge 22. The lower surface 23 of the lower plate 16 is flat and parallel to the flat, outer part of the upper surface 21.

The upper plate 17 has a flat upper surface 30 but its lower surface 31 is formed with a convex, smoothly-curved profile extending across the entire lower surface. The diameter of the upper plate 17 is slightly greater than the diameter d of the cavity 20. The convex profile is also of a part-spherical shape and its radius of curvature is typically about 20 mm, that is, it is greater than that of the cavity 20 so that the curve is shallower than that of the cavity. The centre of curvature of the surface 31 is located directly above that of the cavity 20. It can be seen, therefore, when the upper plate 17 is lowered into contact with the lower plate 16, that the lower surface 31 of the upper plate contacts the lower plate at a circular line of contact, around the edge 22. Because the curvature of the cavity 20 is greater than that of the lower surface 31 of the upper plate 17, the cavity, when closed, resembles the shape of a positive meniscus lens, being deepest at the centre and becoming thinner towards the edges. Typically, the depth of the cavity 20 at the centre, when closed is about 0.5 mm. The outer surfaces 23 and 30 of the cell 11 are flat but they could be formed with spherical lens surfaces so that they can provide a part of the optical system, such as to collimate or focus the beam of radiation. For example, the upper surface 30 of the upper plate 17 could be concave with the same centre of curvature as its lower surface, as shown by the broken line 30' in FIG. 2. This would make the system insensitive to small changes in orientation of the upper element 17 when it is removed and replaced.

The separation, in the cavity 20, between the upper surface 21 of the lower plate 16 and the lower surface 31 of the upper plate 17 is accurately reproducible. The liquid sample 14 is readily placed in the cavity 20 with the upper plate 17 in a raised position and it is then lowered, contacting the liquid first in the centre so that no gas bubbles are formed. Any excess liquid is displaced to the side. When the upper plate 17 is pressed into contact with the lower plate 16, the cavity 20 is closed and the liquid sample 15 is in optical contact across the entire cavity with both the upper and lower plates, thereby forming an efficient optical transmission cell 11.

It can be seen that the smooth concave shape of the cavity 20 enables it to be filled and to be cleaned easily after use since there are no crevices in which the sample 14 can be trapped.

Different pathlengths can be produced readily simply by providing interchangeable upper elements with different radii of curvature.

Figure 4:
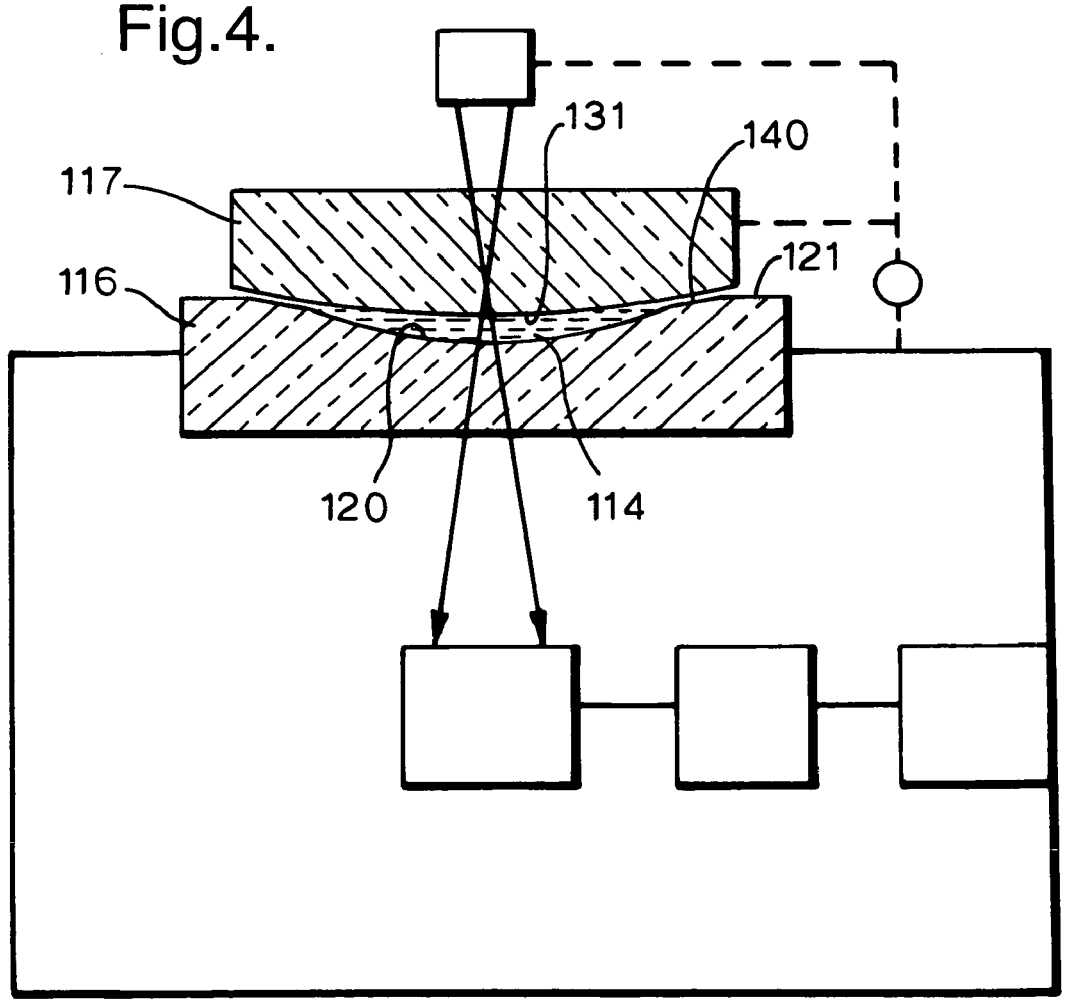
FIG. 4 is a schematic, side elevation view of a second embodiment of apparatus according to the present invention.
Figure 5:
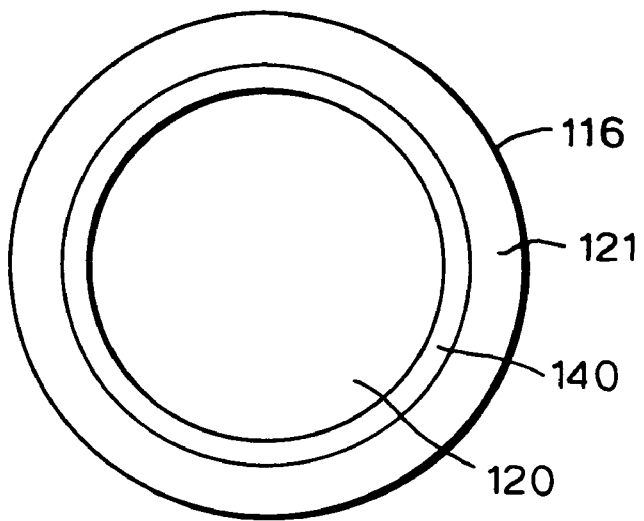
FIG. 5 is a plan view of the lower part of the sampling cell shown in FIG. 4.

The upper element need not contact the lower element at a sharp edge, as in the arrangement of FIGS. 2 and 3, instead an arrangement of the kind shown in FIGS. 4 and 5 could be used. In this, the upper plate 117 has the same shape as before but the upper surface 121 of the lower plate 116 is modified by the addition of a narrow annular band or contact land 140 extending around the outside of the cavity 120. The contact land 140 is curved with the same profile as that of the lower surface 131 of the upper plate 117 so that, when the upper plate is pressed into contact with the lower plate 116, the land seals with the upper plate around the edge of the cavity. This helps retain the sample 114 in the cavity 120, which can be particularly useful with samples containing volatile components.

Figure 6:
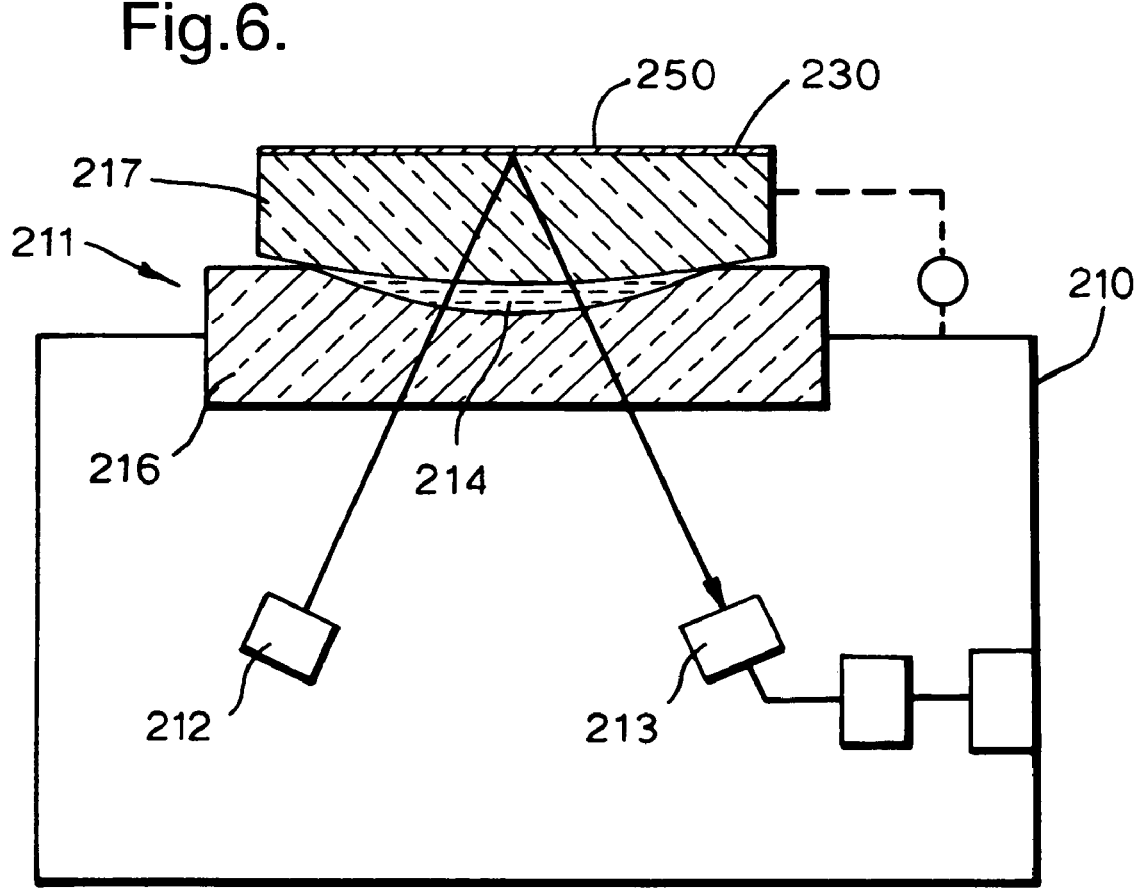
FIG. 6 is a side elevation view of modified apparatus.

In the arrangement shown in FIG. 6, the upper surface 230 of the upper element 217 is coated with a layer 250 of a material that is reflective at the wavelength of the radiation of interest. The radiation source 212 is located below the sample cell 211, within the housing 210 and directs a beam of radiation upwardly at an angle away from the axis of the cell through the lower plate 216, through the thickness of the liquid sample 214 and into the upper plate 217 where it is reflected back by the layer 250 through the thickness of the sample and the lower plate to the detector 213. It can be seen that, in this arrangement, the radiation makes two passes through the thickness of the sample 214. The beam diameters are kept as small as possible to avoid problems from the variation in pathlength across the beam. The variation in pathlength can, however, be an advantage by helping to avoid interference fringes that can arise from parallel surfaces. This arrangement has an advantage that the optical source 212, the detector 213 and the entire optical path through air can be contained within the housing 210. The housing 210 can, therefore, be sealed with a gas-tight seal and the interior of the housing can be purged with a dry gas. This avoids problems that can arise in the infrared region caused by variations in the water vapour content of ambient air. It can also be useful where the sample needs to be heated or cooled, such as to melt more viscous materials or to stabilize the temperature for quantative accuracy. By using a material of high thermal conductivity, such as sapphire, for the lower element 216 and maintaining a low thermal mass for the upper element 217, the sample 214 can be thermally stabilized quickly. The heating or cooling system can be confined to the lower element 216 in the apparatus housing 210 to simplify the design and make it suitable for use in hazardous areas.

Figure 7:
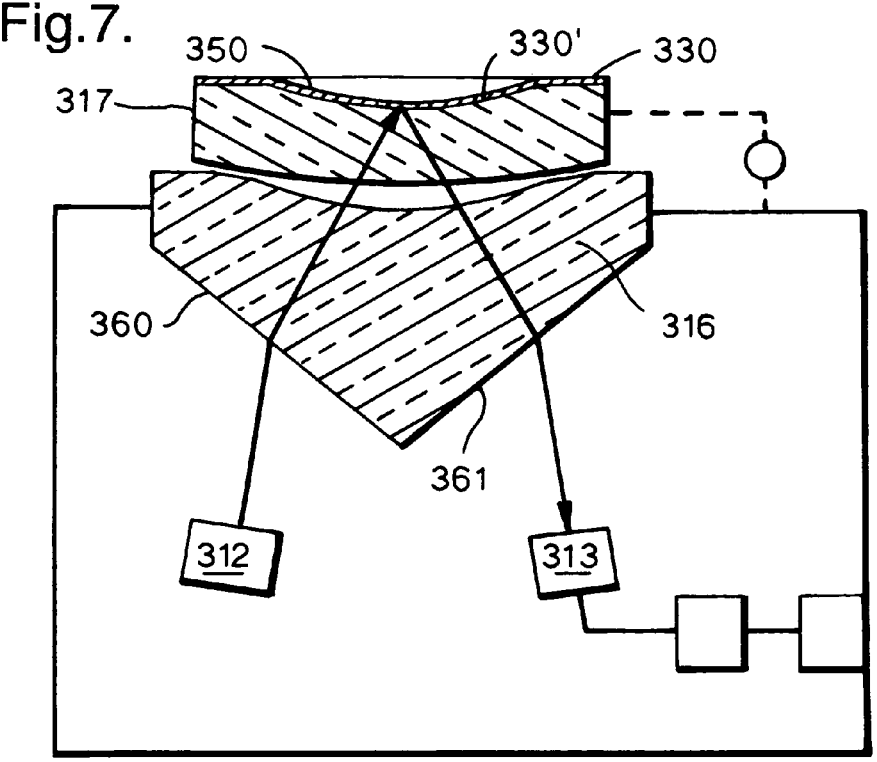
FIG. 7 is a side elevation view of another modified apparatus.

It is not essential for the lower surface of the lower element to be flat. Instead, the lower surface could have a curved profile or it could be angled in the manner shown in FIG. 7 where the lower element 316 is in the form of a right-angle prism with two lower faces 360 and 361 inclined at 90° to one another. The radiation source 312 is located to direct a beam of radiation into the left-hand lower face 360 at an angle away from the normal so that it is refracted into the element 316. Similarly, the detector 313 is located to receive the beam emerging from the right-hand lower face 361 after refraction. This arrangement eliminates any back surface reflections from the output path, which is important in eliminating interference fringing from the measured spectrum. The upper surface 330 of the upper element 317 is coated with a reflective layer 350 and is formed with a central concave recess 330'. This further helps eliminate unwanted beams and reduces the sensitivity of the system to small changes in orientation of the upper element 317.

The arrangements of the present invention can have various advantages. The cell is easy to fill and, when closed, helps eliminate air bubbles. The direct, mechanical contact of the upper and lower elements ensures an accurate and reproducible pathlength. The system can be used with viscous materials, even when using short pathlengths. In addition to liquids, the apparatus can accept some types of semi-solids, such as slurries, waxes, gels, pastes, putties and the like. The apparatus can easily be heated, cooled or thermally stabilized. By heating the cell, solid samples with a low melting point can be tested. The cell is very easy to clean, even with viscous and sticky samples. A disposable alcohol-impregnated wipe may be all that is needed to clean the cell before the next sample. Only small quantities of sample are needed and many can be wiped off with a tissue after measurement.

Figure 8:
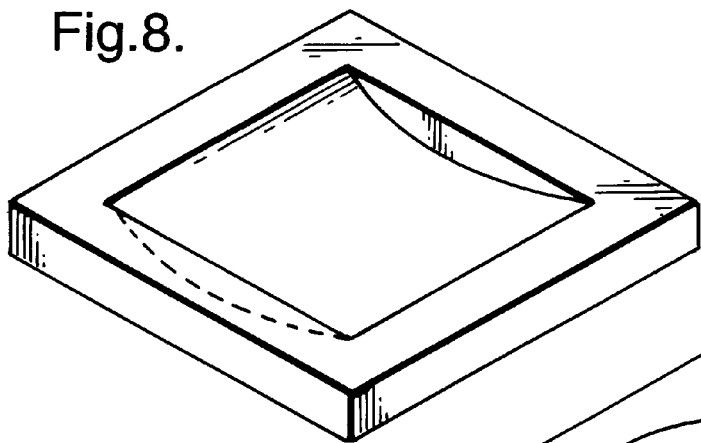
FIG. 8 is a perspective view of the upper surface of a further modified lower element.
Figure 9:
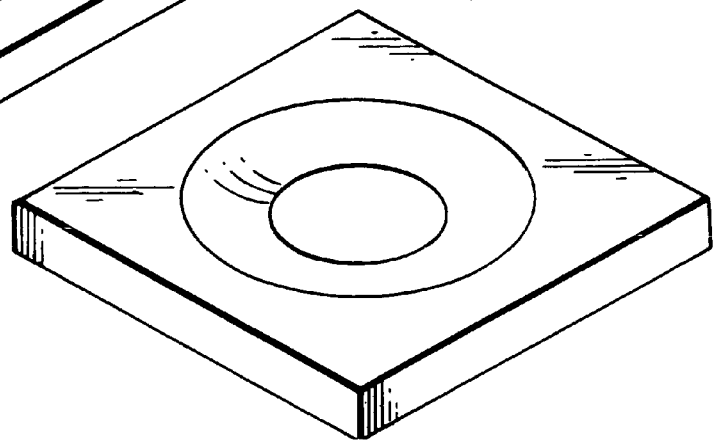
FIG. 9 is a perspective view of the upper surface of a fifth modified lower element.

In the arrangements described above, the cavity in which the sample is contained is of circular shape when viewed in plan. Alternative shapes are, however, possible, such as of a part cylindrical shape, as shown in FIG. 8, or an annular shape, as shown in FIG. 9. In such arrangements, it will be appreciated that the upper element would have a matching shape but with a shallower curve.

Although, in the arrangements described above, both the upper and lower elements are of optically-transparent material, it is only essential for one of these to be transparent. For example, in a reflective system, the lower element could be transparent and the upper element could be opaque with a reflective lower surface. Radiation from a source below the lower element would pass through the lower element into the sample and be reflected by the lower surface of the upper element back through the sample and the lower element to a detector below the cell. The material from which the upper element is formed would, of course, have to be non-reactive with the samples to be tested.

It is not essential for the apparatus to include a radiation source and detector, instead, an external source and detector could be used, the apparatus having mirrors or the like to direct the radiation into and out of the cell. Fibre-optics could be used to bring radiation into or out of the cell.

The apparatus could be provided as a flow cell, having an inlet and outlet by which liquid enters and leaves the cell cavity. The cylindrical shape cavity shown in FIG. 8 may be particularly useful in flow cell applications since the inlet and outlet could be located at opposite ends of an elongate cavity. The detector could be of the imaging kind, such as including an array of detector elements.

What we claim is:

1. An optical sampling arrangement comprising: a first element having an upper surface with a smoothly curved concave cavity in which a liquid sample can be placed; and a second element having a lower surface with a smoothly curved convex formation adapted to locate with said cavity and contact an upper surface of the liquid sample in said cavity thereby reducing the formation of gas bubbles in the liquid sample, wherein said convex formation has a curvature shallower than that of said concave cavity, and at least one of said first and second elements is transparent to optical radiation such that optical radiation can be directed through a thickness of said liquid sample.

2. An optical sampling arrangement according to claim 1, wherein both said first and second elements are optically transparent.

3. An optical sampling arrangement according to claim 1, wherein said cavity is circular in a plane of an upper surface of said first element.

4. An optical sampling arrangement according to claim 1, wherein said first and second elements contact one another along a line of contact at an intersection of said cavity with said upper surface.

5. An optical sampling arrangement according to claim 1, wherein said upper surface of said first element is provided with a contact land around said cavity having a curvature parallel with that of said convex formation such that said convex formation makes contact with said contact land.

6. An optical sampling arrangement according to claim 1, wherein said first element has a lower surface that is flat and parallel with its said upper surface.

7. An optical sampling arrangement according to claim 1, wherein said first element has a lower surface provided with angled faces.

8. An optical sampling arrangement according to claim 7, including a source of radiation arranged to direct radiation into one of said angled faces at an angle to a normal to said face.

9. An optical sampling arrangement according to claim 7, including a radiation detector, said radiation detector being arranged to receive radiation transmitted through a said angled face at an angle to the normal to said face.

10. An optical sampling arrangement according to claim 1, wherein the upper surface of the second element is flat.

11. An optical sampling arrangement according to claim 1, wherein the upper surface of the second element has a curved profile.

12. An optical sampling according to claim 11, wherein the upper surface of the second element is concave with the same center of curvature as the convex surface on the lower surface of the second element.

13. An optical sampling arrangement according to claim 1, wherein the first element is mounted below said second element in a fixed position, and wherein said second element is movable up and down with respect to the first element.

14. An optical sampling according to claim 1, wherein said surfaces of both said first and second elements are transparent.

15. An optical sampling arrangement according to claim 1, wherein one of said elements has a reflective layer on an outer surface arrange to reflect optical radiation back through said element.

16. An optical sampling arrangement according to claim 1, wherein said second element has a reflective surface arranged to reflect optical radiation passing through said first element from below and through said sample back, down through said sample and the first element.

17. An optical sampling arrangement according to claim 1, wherein the optical radiation is in the near infrared region.

18. An optical sampling arrangement according to claim 1, wherein one or both said elements are of sapphire.

19. An optical sampling arrangement according to claim 1, wherein said concave cavity and said convex surface formation are part spherical.

20. An optical sampling arrangement according to claim 1, wherein the concave cavity is closed by engagement by the convex formation about the periphery of the concave cavity.

21. An optical sampling arrangement comprising: a first infra-red transparent base plate with an upper surface with a smoothly curved concave cavity; a second infra-red transparent upper plate having a lower surface with a smoothly curved convex formation having a radius of curvature greater than that of said cavity, wherein said upper plate is movable relative to said base plate to allow a liquid sample to be placed in said cavity and to allow the upper plate to be lowered to contact the upper surface of the liquid sample and the upper surface of said base plate and locate with said cavity thereby reducing the formation of gas bubbles in the liquid sample; and a source of infra-red radiation arranged to direct radiation through both plates and through the liquid sample.

22. An optical sampling arrangement according to claim 21, wherein the concave cavity is closed by engagement by the convex formation about the periphery of the concave cavity.

23. Spectroscopic apparatus including a source of optical radiation, a radiation detector and an optical sampling arrangement located in an optical path between the source and the detector, wherein said optical sampling arrangement comprises: a first element having an upper surface with a smoothly curved concave cavity in which a liquid sample can be placed; and a second element having a lower surface with a smoothly curved convex formation adapted to locate with said cavity and contact an upper surface of the liquid sample in said cavity thereby reducing the formation of gas bubbles in the liquid sample, wherein said convex formation has a curvature shallower than that of said concave cavity, and at least one of said first and second elements is transparent to optical radiation such that optical radiation can be directed through a thickness of said liquid sample.

24. Spectroscopic apparatus according to claim 23, wherein said source of optical radiation is in the near infrared and said detector is responsive to radiation in the near infrared.

25. Spectroscopic apparatus to claim 23, wherein said source and said detector are located on opposite sides of said optical sampling arrangement.

26. Spectroscopic apparatus according to claim 23, wherein said source and detector are located on the same side of said optical sampling arrangement.

27. Spectroscopic apparatus according to claim 26, including a housing containing said source and said detector, and wherein said first element is sealed in an upper surface of said housing.

28. A spectroscopic apparatus according to claim 23, wherein the concave cavity is closed by engagement by the convex formation about the periphery of the concave cavity.

\* \* \* \* \*